United States Patent
Kruck et al.

(10) Patent No.: US 11,957,779 B2
(45) Date of Patent: Apr. 16, 2024

(54) AGENT FOR DYEING KERATINOUS MATERIAL, CONTAINING AMINOSILICONE, PIGMENT AND POLYSACCHARIDE

(71) Applicant: Henkel AG & Co. KGaA, Duesseldorf (DE)

(72) Inventors: Constanze Kruck, Grevenbroich (DE); Sandra Hilbig, Bochum (DE); Melanie Moch, Dormagen (DE); Susanne Dickhof, Viersen (DE); Daniela Kessler-Becker, Leverkusen (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 0 days.

(21) Appl. No.: 17/780,003

(22) PCT Filed: Sep. 16, 2020

(86) PCT No.: PCT/EP2020/075880
§ 371 (c)(1),
(2) Date: May 25, 2022

(87) PCT Pub. No.: WO2021/104706
PCT Pub. Date: Jun. 3, 2021

(65) Prior Publication Data
US 2023/0012032 A1   Jan. 12, 2023

(30) Foreign Application Priority Data
Nov. 26, 2019   (DE) .......................... 102019218234.8

(51) Int. Cl.
| | |
|---|---|
| *A61Q 5/10* | (2006.01) |
| *A61K 8/34* | (2006.01) |
| *A61K 8/73* | (2006.01) |
| *A61K 8/898* | (2006.01) |

(52) U.S. Cl.
CPC .............. *A61K 8/898* (2013.01); *A61K 8/342* (2013.01); *A61K 8/731* (2013.01); *A61K 8/737* (2013.01); *A61Q 5/10* (2013.01)

(58) Field of Classification Search
CPC ........ A61K 8/898; A61K 8/342; A61K 8/731; A61K 8/737; A61K 2800/30; A61K 8/73; A61K 8/732; A61K 8/733; A61Q 5/10; A61Q 5/065
USPC ............................................................ 8/405
See application file for complete search history.

(56) References Cited

U.S. PATENT DOCUMENTS

| | | | | |
|---|---|---|---|---|
| 2010/0083446 A1* | 4/2010 | Brun | ....................... | A61K 8/891 8/405 |
| 2011/0104094 A1* | 5/2011 | Lee | .......................... | A61Q 5/065 424/70.11 |
| 2017/0172901 A1* | 6/2017 | Kerl | ......................... | A61K 8/22 |

FOREIGN PATENT DOCUMENTS

| | | | |
|---|---|---|---|
| DE | 102013226102 A1 | 6/2015 | |
| DE | 102018222022 A1 * | 6/2020 | ............... A61Q 5/10 |
| EP | 3058935 A1 | 8/2016 | |
| FR | 2944967 A1 | 11/2010 | |
| WO | 2011128255 A1 | 10/2011 | |
| WO | WO 2017108828 A1 * | 6/2017 | ............... A61Q 5/06 |

OTHER PUBLICATIONS

Mintel: "Hair Spray", Record ID 5238685, Nov. 2017, Mintel.com.
Udo Peetz, Wacker-Besil ADM Grades: "Creating Tomorrow's Solutions", Record ID XP055206796, Jan. 1, 2004.

* cited by examiner

*Primary Examiner* — Eisa B Elhilo
(74) *Attorney, Agent, or Firm* — Lorenz & Kopf, LLP

(57) ABSTRACT

It is an object of the present disclosure to provide an agent for coloring keratinous material,
   in particular human hair, comprising
   (a1) at least one linear amino-functionalized silicone polymer, and
   (a2) at least one pigment, and
   (a3) at least one polysaccharide,
   exemplified in that the agent is free of silicone resins.
A second subject matter is a method for dyeing keratin material, wherein the agent is applied to the keratin material.

18 Claims, No Drawings

AGENT FOR DYEING KERATINOUS MATERIAL, CONTAINING AMINOSILICONE, PIGMENT AND POLYSACCHARIDE

CROSS-REFERENCE TO RELATED APPLICATION

This application is a U.S. National-Stage entry under 35 U.S.C. § 371 based on International Application No. PCT/EP2020/075880, filed Sep. 16, 2020, which was published under PCT Article 21(2) and which claims priority to German Application No. 10 2019 218 234.8, filed Nov. 26, 2019, which are all hereby incorporated in their entirety by reference.

TECHNICAL FIELD

The subject of the present application is an agent for coloring keratinous material, in particular human hair, which comprises at least one linear, amino-functionalized silicone polymer (a1), at least one pigment (a2) and at least one polysaccharide (a3). Furthermore, the agent is exemplified by being free of silicone resins.

A second object of this application is a method for dyeing keratinous material, in particular human hair, wherein an agent of the first object of the present disclosure is applied to the keratinous material, allowed to act and then washed out again with water.

BACKGROUND

Changing the shape and color of keratinous material, especially human hair, is a key area of modern cosmetics. To change the hair color, the expert knows various coloring systems depending on the coloring requirements. Oxidation dyes are usually used for permanent, intensive dyeings with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeings obtained with direct dyes have a shorter shelf life and quicker wash ability. Dyes with direct dyes usually remain on the hair for a period of between 5 and about 20 washes.

The use of color pigments is known for short-term color changes on the hair and/or skin. Color pigments are understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeings, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes. One viable alternative coloring system that has recently come increasingly into focus is based on the use of colored pigments.

BRIEF SUMMARY

Agents and methods for dyeing keratinous material are provided. In an exemplary embodiment, an agent for dyeing keratinous material includes at least one linear amino-functionalized silicone polymer (a1), at least one pigment (a2), and at least one polysaccharide (a3). The agent is also free of silicone resins.

A method for dyeing keratinous material is provided in another embodiment. The method includes applying an agent to the keratinous material, where the agent includes at least one linear amino-functionalized silicone polymer (a1), at least one pigment (a2), and at least one polysaccharide (a3). The agent is also free of silicone resins. The agent is exposed to the keratinous material, and then the agent is rinsed out of the keratinous material with water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Coloring with pigments offers several significant advantages. Since the pigments only attach themselves to the keratin materials, especially the hair fibers, from the outside, the damage associated with the dyeing process is particularly low. Furthermore, colorations that are no longer desired can be removed quickly and easily without leaving any residue, thus offering the user the possibility of returning to his original hair color immediately and without significant effort. Especially for those consumers who do not want to recolor their hair regularly, this coloring process is therefore particularly attractive.

In recent work, the problem of low durability of this staining system has been addressed. In this context, it was found that the wash fastness of the color results obtained with pigments could be improved by combining the pigments with certain amino-functionalized silicone polymers. Despite the possibilities thus found to improve wash fastness or color retention, there is still a need for optimization in this context. Particularly for eye-catching and fashionable shades, a way is sought to improve the color intensity even further.

Pigment-based dyeing systems are described, for example, in EP 3058935 B1. To improve the deposition of pigments on hair and to produce natural-looking colorations, EP 3058935 B1 proposes the use of a formulation that further contains, in an aqueous-alcoholic base, an amino silicone, a silicone resin and a thickener system of various polymers, in addition to a pigment.

In reworking the teaching of EP 3058935 B1, it has now been shown that the silicone resins contained in the agent can also have a detrimental effect on the colored hair. Firstly, the silicone resins have been shown to significantly worsen the feel of dyed hair. Furthermore, it has also been found that the corresponding colorants with silicone resins are clearly inferior also regarding color intensity.

It was the task of the present disclosure to provide a coloring system with which pigments can be fixed to the hair in as permanent a manner as possible. The use of this dyeing system should achieve particularly intensive dyeing results with good fastness properties. At the same time, the hair should feel as pleasant to the touch as possible and should not feel greasy, weighed down, dull or coated.

Surprisingly, it has now been found that the problem can be excellently solved if keratinous materials, in particular hair, are colored with an agent containing at least one linear amino-functionalized silicone polymer (a1), at least one pigment (a2) and at least one polysaccharide (a3). Furthermore, test series have shown that good coloring effects were obtained when the corresponding agents were free from silicone resins.

A first object of the present disclosure is an agent for coloring keratinous material, in particular human hair, comprising.
(a1) at least one linear amino-functionalized silicone polymer, and
(a2) at least one pigment, and
(a3) at least one polysaccharide,
exemplified in that the agent is free of silicone resins.

In the course of the work conducted on the present disclosure, it has been surprisingly shown that the use of a polysaccharide (a3) in an agent containing an amino silicone (a1), and a pigment (a2) and a fatty component (a4), leads to an increase in color intensity when this agent is applied in a dyeing process on the keratinous material, on human hair. The agent had to be free of silicone resins.

Keratinic Material

Keratinous material includes hair, skin, nails (such as fingernails and/or toenails). Wool, furs and feathers also fall under the definition of keratinous material. Preferably, keratinous material is understood to be human hair, human skin and human nails, especially fingernails and toenails. Keratinous material is understood to be human hair.

Coloring Agent

The term "coloring agent" is used in the context of the present disclosure for a coloring of the keratin material, of the hair, caused using coloring compounds, in particular pigments. In this coloring process, the pigments are deposited as coloring compounds in a particularly homogeneous, uniform and smooth film on the surface of the keratin material.

Linear Amino-Functionalized Silicone Polymers (a1)

As the first ingredient (a1) essential to the present disclosure, the agent contains at least one linear amino-functionalized silicone polymer. The amino-functionalized silicone polymer may alternatively be referred to as amino silicone or amodimethicone.

Silicone polymers are macromolecules with a molecular weight of at least about 500 g/mol, preferably at least about 1000 g/mol, more preferably at least about 2500 g/mol, particularly preferably at least about 5000 g/mol, which comprise repeating organic units.

The maximum molecular weight of the silicone polymer depends on the degree of polymerization (number of polymerized monomers) and the batch size and is partly determined by the polymerization method. As contemplated herein, it is preferred if the maximum molecular weight of the silicone polymer is not more than about $10^7$ g/mol, preferably not more than about $10^6$ g/mol, and particularly preferably not more than about 105 g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than about 10 Si—O repeat units, preferably more than about 50 Si—O repeat units, and more preferably more than about 100 Si—O repeat units, most preferably more than about 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

A linear silicone polymer is understood to be a linear polymer without branches, including only one polymer chain, the main chain.

In other words, a linear amino-functionalized silicone polymer is a polysiloxane of the type (Si-linear)

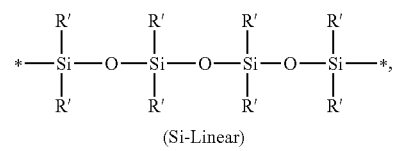

(Si-Linear)

i.e., the radicals R' located on the silicon atoms may represent (in each case independently of one another) organic radicals such as methyl groups, $C_1$-$C_{20}$ alkyl groups, amino-$C_1$-$C_{20}$ alkyl groups or substituted $C_1$-$C_{20}$ alkyl groups, but the siloxane main chain itself formed by the sequence of silicon atoms and oxygen atoms is not indicated and is therefore linear.

In principle, beneficial effects could be obtained with linear amino-functionalized silicone polymers (a1) if they carry at least one primary, at least one secondary and/or at least one tertiary amino group. However, dyeings with the best wash fastness were observed when a linear amino-functionalized silicone polymer (a1) was used in agent (a), which contains at least one secondary amino group.

In a very particularly preferred embodiment, a process as contemplated herein is exemplified in that the agent (a) comprises at least one linear amino-functionalized silicone polymer (a1) having at least one secondary amino group.

The secondary amino group(s) may be located at various positions on the amino-functionalized silicone polymer. Particularly beneficial effects were found when an amino-functionalized silicone polymer (a1) was used that has at least one, preferably several, structural units of the formula (Si amino).

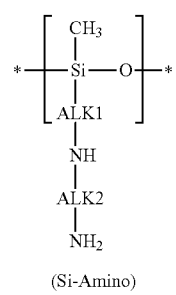

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, a process as contemplated herein is exemplified in that the agent (a) comprises at least one linear amino-functionalized silicone polymer (a1) comprising at least one structural unit of the formula (Si amino),

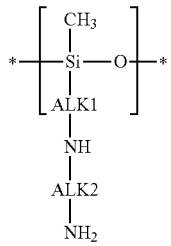

(Si-Amino)

where
ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A bivalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In another particularly preferred embodiment, the structural units of the formula (Si amino) represent repeat units in the linear amino-functionalized silicone polymer (a1), such that the silicone polymer comprises multiple structural units of the formula (Si amino).

Particularly well-suited amino-functionalized silicone polymers (a1) with at least one secondary amino group are listed below.

Dyeings with the best wash fastnesses could be obtained if, in the process as contemplated herein, at least one agent (a) containing at least one linear amino-functionalized silicone polymer (a1) comprising structural units of the formula (Si-I) and of the formula (Si-II) was applied to the keratinous material.

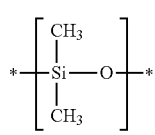

(Si-I)

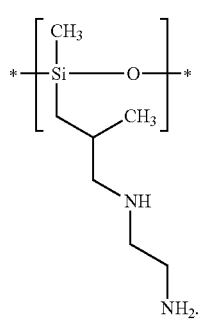

(Si-II)

In another explicitly quite particularly preferred embodiment, a process as contemplated herein is exemplified in that the agent (a) contains at least one linear amino-functionalized silicone polymer (a1) comprising structural units of the formula (Si-I) and of the formula (Si-II).

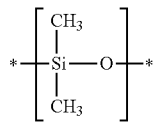

(Si-I)

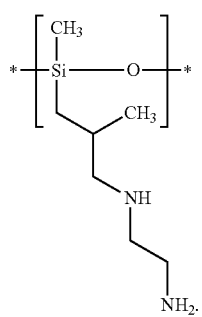

(Si-II)

A corresponding amino functionalized silicone polymer with the structural units (Si-I) and (Si-II) is, for example, the commercial product DC 2-8566 or Dowsil® 2-8566 Amino Fluid, which is commercially distributed by the Dow® Chemical Company and bears the designation "Siloxanes and Silicones, 3-[(2-aminoethyl)amino]-2-methylpropyl Me, Di-Me-Siloxane" and the CAS number 106842-44-8.

In the context of a further preferred embodiment, a process as contemplated herein is exemplified by the application of an agent (a) to the keratinous material, the agent (a) comprising at least one amino-functional silicone polymer (a1) of the formula of formula (Si-III),

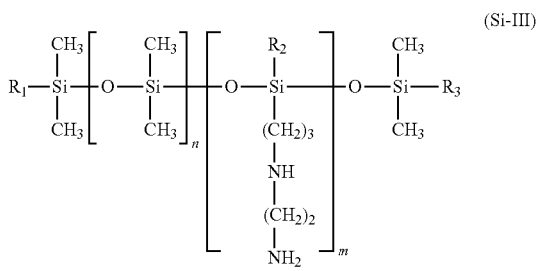

(Si-III)

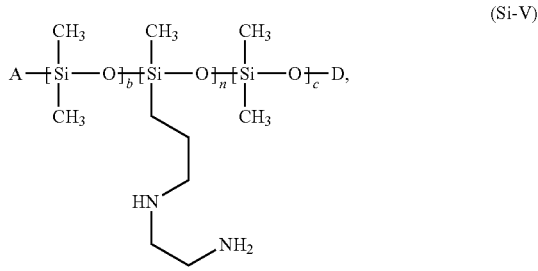

(Si-V)

where m and n mean numbers chosen so that the sum (n+m) is in the range 1 to about 1000, n is a number in the range 0 to 999 and m is a number in the range 1 to about 1000, R1, R2 and R3, which are the same or different, denote a hydroxy group or a C1-4 alkoxy group, wherein at least one of R1 to R3 represents a hydroxy group.

Further methods preferred as contemplated herein are exemplified by the application of an agent (a) to the keratinous material, the agent (a) comprising at least amino-functional silicone polymer (a1) of the formula of formula (Si-IV),

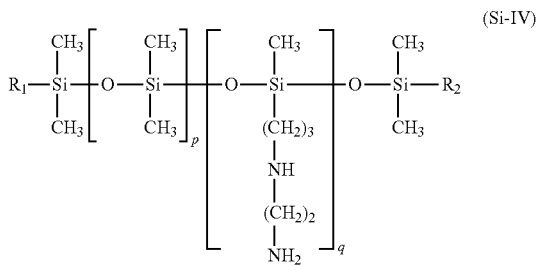

(Si-IV)

where p and q mean numbers chosen so that the sum (p+q) is in the range 1 to about 1000, p is a number in the range 0 to 999 and q is a number in the range 1 to about 1000, R1 and R2, which are different, denote a hydroxy group or a $C_1$-4 alkoxy group, at least one of R1 to R2 denoting a hydroxy group.

The silicones of the formulas (Si-III) and (Si-IV) differ in the grouping at the Si atom, which carries the nitrogen-containing group: In formula (Si-III), R2 represents a hydroxy group or a C1-4 alkoxy group, while the radical in formula (Si-IV) is a methyl group. The individual Si groupings, which are marked with the indices m and n or p and q, do not have to be present as blocks; rather, the individual units can also be present in a statistically distributed manner, i.e. in the formulas (Si-III) and (Si-IV), not every R1-Si (CH$_3$)$_2$ group is necessarily bonded to an —[O—Si(CH$_3$)$_2$] grouping.

Processes as contemplated herein in which an agent (a) containing at least one linear amino-functional silicone polymer (a1) of the formula of the formula (Si-V) is applied to the keratin fibers have also proved to be particularly effective regarding the desired effects.

where

A represents a group —OH, —O—Si(CH$_3$)$_3$, —O—Si (CH$_3$)$_2$OH, —O—Si(CH$_3$)$_2$OCH$_3$, D represents a group —H, —Si(CH$_3$)$_3$, —Si(CH$_3$)$_2$OH, —Si(CH$_3$)$_2$OCH$_3$, b, n and c stand for integers between 0 and about 1000, with the specifications n>0 and b+c>0 at least one of the conditions A=-OH or D=-H is fulfilled.

In the above formula (Si-V), the individual siloxane units are statistically distributed with the indices b, c and n, i.e., they do not necessarily have to be block copolymers.

Agent (a) may further comprise one or more different amino-functionalized silicone polymers represented by the formula (Si-VI)

$$M(R_aQ_bSiO_{(4-a-b)/2})_x(R_cSiO_{(4-c)/2})_yM \qquad (Si\text{-}VI)$$

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical containing at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2,000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3- chloropropyl, 4-bromobutyl, 3,3,3-trifluoropropyl, chlorocyclohexyl, bromophenyl, chlorophenyl and the like, and sulfur-containing radicals, such as mercaptoethyl, mercaptopropyl, mercaptohexyl, mercaptophenyl and the like; preferably R is an alkyl radical containing from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$ CH$_2$CH$_2$—, —CH$_2$CH(CH$_3$)C (O)OCH₂—, —(CH₂)₃CC(O)OCH₂CH₂—, —C₆H₄C₆H₄—, —C₆H₄CH₂C₆H₄—; and —(CH₂)₃C(O)SCH₂CH₂—.

Z is an organic amino functional radical containing at least one amino functional group. One formula for Z is NH(CH₂)$_z$NH₂, where z is 1 or more. Another formula for Z is —NH(CH₂)$_z$(CH₂)$_{zz}$NH, wherein both z and zz are independently 1 or more, this structure comprising diamino ring structures, such as piperazinyl. Z is most preferably an —NHCH₂CH₂NH₂ radical. Another formula for Z is —N(CH₂)$_z$(CH₂)$_{zz}$NX₂ or —NX₂, wherein each X of X2 is independently selected from the group of hydrogen and alkyl groups having 1 to about 12 carbon atoms, and zz is 0.

Q is most preferably a polar, amine-functional radical of the formula —CH₂CH₂CH₂NHCH₂CH₂NH₂. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$SiO$_{(4-a-b)/2}$ units to R$_c$SiO$_{(4-c)/2}$ units is in the range of about 1:2 to about 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, a method as contemplated herein is exemplified by the application of an agent (a) to the keratinous material, wherein the agent (a) contains an amino-functional silicone polymer of formula (Si-VII)

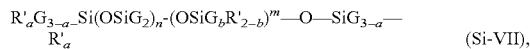
(Si-VII), wherein:
G is —H, a phenyl group, —OH, —O—CH₃, —CH₃, —O—CH₂CH₃, —CH₂CH₃, —O—CH₂CH₂CH₃, —CH₂CH₂CH₃, —O—CH(CH₃)₂, —CH(CH₃)₂, —O—CH₂CH₂CH₂CH₃, —CH₂CH₂CH₂CH₃, —O—CH₂CH(CH₃)₂, —CH₂CH(CH₃)₂, —O—CH(CH₃)CH₂CH₃, —CH(CH₃)CH₂CH₃, —O—C(CH₃)₃, —C(CH₃)₃;
a stands for a number between 0 and 3, especially 0;
b stands for a number between 0 and 1, especially 1,
m and n are numbers whose sum (m+n) is between 1 and about 2000, preferably between about 50 and about 150, where n preferably assumes values from 0 to about 1999 and from about 49 to about 149 and m preferably assumes values from 1 to about 2000, from 1 to about 10,
R' is a monovalent radical selected from
-Q-N(R")—CH₂—CH₂—N(R")₂
-Q-N(R")₂
-Q-N+(R")₃A⁻
-Q-N+H(R")₂A⁻
-Q-N+H₂(R")A⁻
-Q-N(R")—CH₂—CH₂—N+R"H₂A⁻,
where each Q is a chemical bond, —CH₂—, —CH₂—CH₂—, —CH₂CH₂CH₂—, —C(CH₃)₂—, —CH₂CH₂CH₂CH₂—, —CH₂C(CH₃)₂—, or —CH(CH₃)CH₂CH₂—,
R" represents identical or different radicals selected from the group of —H, -phenyl, -benzyl, —CH₂—CH(CH₃)Ph, the C$_{1-20}$ alkyl radicals, preferably —CH₃, —CH₂CH₃, —CH₂CH₂CH₃, —CH(CH₃)₂, —CH₂CH₂CH₂H₃, —CH₂CH(CH₃)₂, —CH(CH₃)CH₂CH₃, —C(CH₃)₃, and A represents an anion preferably selected from chloride, bromide, iodide or methosulfate.

In the context of a further preferred embodiment, a process as contemplated herein is exemplified by the application of an agent (a) to the keratinous material, the agent (a) comprising at least one amino-functional silicone polymer (a1) of the formula (Si-VIIa),

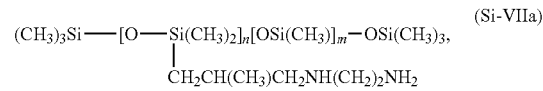
(Si-VIIa)

wherein m and n are numbers whose sum (m+n) is between 1 and about 2000, preferably between about 50 and about 150, n preferably assuming values from 0 to about 1999 and from about 49 to about 149, and m preferably assuming values from 1 to about 2000, from 1 to about 10.

According to the INCI declaration, these silicones are called trimethylsilylamodimethicones.

In another preferred embodiment, a method as contemplated herein is exemplified by the application of an agent (a) to the keratinous material, said agent (a) comprising at least one amino-functional silicone polymer of formula (Si-VIIb)

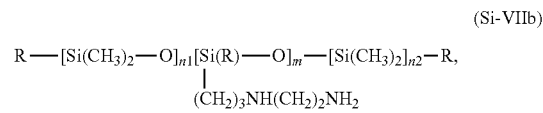
(Si-VIIb)

in which R represents —OH, —O—CH₃ or a —CH₃ group and m, n1 and n2 are numbers whose sum (m+n1+n2) is between 1 and about 2000, preferably between about 50 and about 150, the sum (n1+n2) preferably assuming values from 0 to about 1999 and in particular from about 49 to about 149 and m preferably assuming values from 1 to about 2000, and in particular from 1 to about 10.

According to the INCI declaration, these amino-functionalized silicone polymers are called amodimethicones.

Regardless of which amino-functional silicones are used, agents (a) as contemplated herein are preferred which contain an amino-functional silicone polymer whose amine number is above about 0.25 meq/g, preferably above about 0.3 meq/g and in particular above about 0.4 meq/g. The amine number represents the milliequivalents of amine per gram of the amino-functional silicone. It can be determined by titration and expressed in the unit mg KOH/g.

It has been found to be particularly advantageous if the agent as contemplated herein contains the linear amino-functionalized silicone polymer(s) (a1) in certain ranges of amounts. Particularly satisfactory results were obtained when the agent contains—based on the total weight of the agent—one or more linear amino-functionalized silicone polymer(s) in a total amount of about 0.1 to about 8.0 wt. %, preferably about 0.2 to about 5.0 wt. %, more preferably about 0.3 to about 3.0 wt. % and most preferably about 0.4 to about 2.5 wt. %.

In another particularly preferred embodiment, an agent as contemplated herein is exemplified in that it contains—based on the total weight of the agent—one or more linear amino-functionalized silicone polymers (a1) in a total amount of from about 0.1 to about 8.0 wt. %, preferably from about 0.2 to about 5.0 wt. %, more preferably from about 0.3 to about 3.0 wt. % and very particularly preferably from about 0.4 to about 2.5 wt. %.

Pigments (a2)

As a second essential component, the agent as contemplated herein contains at least pigment.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent as contemplated herein is exemplified in that it comprises at least one colorant compound (a2) from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent as contemplated herein is exemplified in that it contains at least one colorant compound (a2) from the group of inorganic pigments, which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, a composition as contemplated herein is exemplified in that it comprises (a) at least one colorant compound (a2) from the group of pigments selected from mica- or mica-based pigments which are reacted with one or more metal oxides from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck®, Ariabel® and Unipure® from Sensient®, Prestige® from Eckart® Cosmetic Colors and Sunshine® from Sunstar®.

Particularly preferred color pigments with the trade name Colorona® are, for example:

Colorona® Copper, Merck®, MICA, CI 77491 (IRON OXIDES)

Colorona® Passion Orange, Merck®, Mica, CI 77491 (Iron Oxides), Alumina

Colorona® Patina Silver, Merck®, MICA, CI 77499 (IRON OXIDES), CI 77891 (TITANIUM DIOXIDE)

Colorona® RY, Merck®, CI 77891 (TITANIUM DIOXIDE), MICA, CI 75470 (CARMINE)

Colorona® Oriental Beige, Merck®, MICA, CI 77891 (TITANIUM DIOXIDE), CI 77491 (IRON OXIDES)

Colorona® Dark Blue, Merck®, MICA, TITANIUM DIOXIDE, FERRIC FERROCYANIDE Colorona® Chameleon, Merck®, CI 77491 (IRON OXIDES), MICA Colorona® Aborigine Amber, Merck®, MICA, CI 77499 (IRON OXIDES), CI 77891 (TITANIUM DIOXIDE)

Colorona® Blackstar Blue, Merck®, CI 77499 (IRON OXIDES), MICA Colorona® Patagonian Purple, Merck®, MICA, CI 77491 (IRON OXIDES), CI 77891 (TITANIUM DIOXIDE), CI 77510 (FERRIC FERROCYANIDE)

Colorona® Red Brown, Merck®, MICA, CI 77491 (IRON OXIDES), CI 77891 (TITANIUM DIOXIDE)

Colorona® Russet, Merck®, CI 77491 (TITANIUM DIOXIDE), MICA, CI 77891 (IRON OXIDES)

Colorona® Imperial Red, Merck®, MICA, TITANIUM DIOXIDE (CI 77891), D&C RED NO. 30 (CI 73360)

Colorona® Majestic Green, Merck®, CI 77891 (TITANIUM DIOXIDE), MICA, CI 77288 (CHROMIUM OXIDE GREENS)

Colorona® Light Blue, Merck®, MICA, TITANIUM DIOXIDE (CI 77891), FERRIC FERROCYANIDE (CI 77510)

Colorona® Red Gold, Merck®, MICA, CI 77891 (TITANIUM DIOXIDE), CI 77491 (IRON OXIDES)

Colorona® Gold Plus MP 25, Merck®, MICA, TITANIUM DIOXIDE (CI 77891), IRON OXIDES (CI 77491)

Colorona® Carmine Red, Merck®, MICA, TITANIUM DIOXIDE, CARMINE Colorona® Blackstar Green, Merck®, MICA, CI 77499 (IRON OXIDES)

Colorona® Bordeaux, Merck®, MICA, CI 77491 (IRON OXIDES)

Colorona® Bronze, Merck®, MICA, CI 77491 (IRON OXIDES)

Colorona® Bronze Fine, Merck®, MICA, CI 77491 (IRON OXIDES)

Colorona® Fine Gold MP 20, Merck®, MICA, CI 77891 (TITANIUM DIOXIDE), CI 77491 (IRON OXIDES)

Colorona® Sienna Fine, Merck®, CI 77491 (IRON OXIDES), MICA

Colorona® Sienna, Merck®, MICA, CI 77491 (IRON OXIDES)
Colorona® Precious Gold, Merck®, Mica, CI 77891 (Titanium dioxide), Silica, CI 77491 (Iron oxides), Tin oxide
Colorona® Sun Gold Sparkle MP 29, Merck®, MICA, TITANIUM DIOXIDE, IRON OXIDES, MICA, CI 77891, CI 77491 (EU)
Colorona® Mica Black, Merck®, CI 77499 (Iron oxides), Mica, CI 77891 (Titanium dioxide)
Colorona® Bright Gold, Merck®, Mica, CI 77891 (Titanium dioxide), CI 77491 (Iron oxides)
Colorona® Blackstar Gold, Merck®, MICA, CI 77499 (IRON OXIDES)

Other particularly preferred color pigments with the trade name
Xirona® are for example:
Xirona® Golden Sky, Merck®, Silica, CI 77891 (Titanium Dioxide), Tin Oxide
Xirona® Caribbean Blue, Merck®, Mica, CI 77891 (Titanium Dioxide), Silica, Tin Oxide
Xirona® Kiwi Rose, Merck®, Silica, CI 77891 (Titanium Dioxide), Tin Oxide
Xirona® Magic Mauve, Merck®, Silica, CI 77891 (Titanium Dioxide), Tin Oxide.

In addition, particularly preferred color pigments with the trade name
Unipure® are for example:
Unipure® Red LC 381 EM, Sensient® CI 77491 (Iron Oxides), Silica
Unipure® Black LC 989 EM, Sensient®, CI 77499 (Iron Oxides), Silica
Unipure® Yellow LC 182 EM, Sensient®, CI 77492 (Iron Oxides), Silica In a further embodiment, the agent as contemplated herein may also contain one or more colorant compounds (a2) from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyrrole, indigo, thioindigo, dioxazine and/or triarylmethane compounds.

Examples of particularly suitable organic pigments are carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, an agent as contemplated herein is exemplified in that it comprises at least one colorant compound (a2) from the group of organic pigments which is preferably selected from the group of carmine, quinacridone, phthalocyanine, sorghum, blue pigments having the color index numbers Cl 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color lacquer. In the sense of the present disclosure, the term color lacquer means particles comprising a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color lacquer can be used.

Due to their excellent light and temperature resistance, the use of the above pigments in the agent (a) of the process as contemplated herein is particularly preferred. It is also preferred if the pigments used have a certain particle size. As contemplated herein, it is therefore advantageous if the at least one pigment has an average particle size $D_{50}$ of about 1.0 to about 50 μm, preferably about 5.0 to about 45 μm, preferably about 10 to about 40 μm, about 14 to about 30 μm. The average particle size $D_{50}$, for example, can be determined using dynamic light scattering (DLS).

The colorant compounds (a2), the colorant compounds from the group of pigments, represent the second essential part of the agent as contemplated herein and are preferably used in the agent in certain ranges of amounts. Particularly satisfactory results were obtained when the agent contained—based on the total weight of the agent—one or more pigments (a2) in a total amount of about 0.01 to about 10.0 wt. %, preferably about 0.1 to about 5.0 wt. %, further preferably about 0.2 to about 2.5 wt. % and very preferably about 0.25 to about 1.5 wt. %.

In another very particularly preferred embodiment, an agent as contemplated herein is exemplified in that the agent contains—based on the total weight of the agent—one or more pigments (a2) in a total amount of from about 0.01 to about 10.0 wt. %, preferably from about 0.1 to about 5.0 wt. %, more preferably from about 0.2 to about 2.5 wt. % and very particularly preferably from about 0.25 to about 1.5 wt. %.

As a further optional ingredient, the agents of the present disclosure may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes as contemplated herein have a solubility in water (760 mmHg) at 25° C. of more than 0.5 g/L and are therefore not to be regarded as pigments. Preferably, the direct dyes as contemplated herein have a solubility in water (760 mmHg) at 25° C. of more than 1.0 g/L.

Direct dyes can be divided into anionic, cationic and non-ionic direct dyes.

In a further embodiment, a process as contemplated herein is exemplified in that the agent (a) comprises at least one colorant compound (a2) from the group of anionic, non-ionic and cationic direct dyes.

Suitable cationic direct dyes include Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347/Dystar®), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO$^-$, —SO$_3^-$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Acid dyes can also be used in the form of their sodium salts and/or their potassium salts.

The acid dyes as contemplated herein have a solubility in water (760 mmHg) at 25° C. of more than 0.5 g/L and are therefore not to be regarded as pigments. Preferably the acid dyes as contemplated herein have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential feature of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In another embodiment, a process for dyeing keratinous material is exemplified in that the agent (a) comprises at least one anionic direct dye selected from the group of nitrophenylenediamines, nitroaminophenols, azo dyes, anthraquinone dyes, triarylmethane dyes, xanthene dyes, rhodamine dyes, oxazine dyes and/or indophenol dyes, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

Suitable acid dyes may include, for example, one or more compounds selected from the following group: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodium-salt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C-Rot 46, Real red D, FD&C Red Nr.2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiodo-fluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 92 (COLIPA no C$_{53}$, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C$_{063}$), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved radicals, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has an extremely high water solubility of more than 20 wt. %.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a solubility in water of more than 20 wt. % (25° C.).

In a further embodiment, an agent as contemplated herein is therefore exemplified in that it comprises at least one direct dye (a2) selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct-acting dye or dyes can be used in various amounts in the agents, depending on the desired color intensity. Satisfactory results were obtained when the agent contains—based on the total weight of the agent—one or more direct dyes (a2) in a total amount of from about 0.01 to about 10.0 wt. %, preferably from about 0.1 to about 8.0 wt. %, more preferably from about 0.2 to about 6.0 wt. % and most preferably from about 0.5 to about 4.5 wt. %.

Furthermore, the agent may also contain at least one photochromic or thermochromic dye as the coloring compound (a2).

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (Thermochromism).

The agent may contain—based on the total weight of the composition—one or more photochromic dyes (a2) in a total amount of from about 0.01 to about 10.0 wt. %, preferably from about 0.1 to about 8.0 wt. %, more preferably from about 0.2 to about 6.0 wt. % and most preferably from about 0.5 to about 4.5 wt. %.

Polysaccharides (a3)

As a third constituent (a3) essential to the present disclosure, the agents as contemplated herein contain at least one polysaccharide.

The term polysaccharides are the collective term for macromolecular carbohydrates, whose molecules include a large number of glycosidically linked monosaccharide molecules (with a molar mass of at least about 5000 g/mol).

The agents as contemplated herein may contain one or more polysaccharides (a3) selected from the group of nonionic polysaccharides, anionic polysaccharides and cationic polysaccharides.

In a preferred embodiment, an agent as contemplated herein is exemplified in that it comprises at least one polysaccharide (a3) selected from the group of nonionic polysaccharides, anionic polysaccharides and cationic polysaccharides.

Staining results with particularly high intensity could be obtained if at least one polysaccharide (a3) from the group of nonionic polysaccharides and/or anionic polysaccharides was used in the agent as contemplated herein. The use of non-ionic and/or anionic polysaccharides is therefore particularly preferred.

In a particularly preferred embodiment, an agent as contemplated herein is exemplified in that it comprises at least one polysaccharide (a3) selected from the group of nonionic polysaccharides and anionic polysaccharides.

In a preferred embodiment, the agent as contemplated herein comprises at least one nonionic polysaccharide. Within the group of non-ionic polysaccharides, various compounds and derivatives have proved to be very suitable for solving the problem of the present disclosure.

Nonionic polysaccharides selected from the group of hydroxy-$C_1$-$C_{30}$-alkylcelluloses, hydroxy-$C_1$-$C_{30}$-alkylmethylcelluloses, hydroxy-$C_1$-$C_{30}$-alkylethylcelluloses, $C_1$-$C_{30}$-alkylcelluloses and cellulose showed particularly good suitability.

In a particularly preferred embodiment, an agent as contemplated herein is exemplified in that it comprises at least one nonionic polysaccharide (a3) selected from the group of hydroxy-$C_1$-$C_{30}$-alkylcellulose, hydroxy-$C_1$-$C_{30}$-alkylmethylcellulose, hydroxy-$C_1$-$C_{30}$-alkylethylcellulose, $C_1$-$C_{30}$-alkylcellulose, $C_6$-$C_{30}$-alkylhydroxyethylcelluloses, cellulose and starch.

Hydroxy-$C_1$-$C_{30}$-alkyl celluloses are cellulose ethers technically produced by etherification of alkyl cellulose with the corresponding alkylene oxide.

Particularly preferred hydroxy-$C_1$-$C_{30}$ alkyl celluloses are hydroxyethyl cellulose and hydroxypropyl cellulose.

Hydroxyethyl cellulose is a cellulose ether that is technically produced by etherifying alkali cellulose with ethylene oxide. Since the primary hydroxy group of a 2-hydroxyethyl substituent formed in the first etherification step of a cellulose OH group with ethylene oxide reacts with further ethylene oxide faster than the hydroxy groups of cellulose itself, longer oligo or polyethylene oxide side chains are present in the resulting HECs alongside unreacted cellulose OH groups.

A particularly well-suited hydroxyethyl cellulose can be obtained commercially, for example, in the form of the raw material Natrosol® 250 HHX from the Ashland company.

Another particularly well-suited hydroxyethyl cellulose is sold commercially under the trade name Cellosize® WP 300 H by the Dow@ company.

Hydroxypropyl celluloses are cellulose ethers technically produced by reacting alkali celluloses with methyloxirane (propylene oxide). Commercially available hydroxypropyl celluloses are offered with an average molar degree of substitution (MS) of about 4-4.5.

A particularly well-suited hydroxypropyl cellulose can be found, for example, in the form of the raw material Klucel® H CS and can be purchased from the company Hercules®.

In a particularly preferred embodiment, an agent as contemplated herein is exemplified in that it comprises at least one polysaccharide (a3) selected from the group of hydroxyethyl cellulose and hydroxypropyl cellulose.

Hydroxy-$C_1$-$C_{30}$-alkylmethyl celluloses are alkoxylated methyl celluloses.

For example, a very particularly preferred hydroxy-$C_1$-$C_{30}$-alkylmethylcellulose is hydroxyethylmethylcellulose. Hydroxyethylmethylcellulose is a collective term for chemical compounds produced by etherification of cellulose. In these, part of the hydroxy groups of cellulose is linked as ethers with methyl and with hydroxyethyl groups.

Another very particularly preferred hydroxy-$C_1$-$C_{30}$-alkylmethylcellulose is, for example, hydroxypropyl methylcellulose. Hydroxypropyl methylcellulose is a methylcellulose substituted with propylene oxide. It is marketed in various degrees of polymerization and different degrees of substitution.

A particularly well-suited hydroxypropyl methyl cellulose can be obtained commercially, for example, in the form of the product Benecel K 4 M from the company Ashland.

Hydroxy-$C_1$-$C_{30}$-alkylethyl celluloses are alkoxylated ethyl celluloses.

Examples of suitable $C_1$-$C_{30}$ alkyl celluloses include methyl cellulose and ethyl cellulose.

Under the trade names Culminal® DM 40 and Culminal® MC 12000, various Methyl celluloses are available for purchase from the Hercules® company.

Ethyl cellulose is semi synthetically derived from naturally occurring cellulose and is a cellulose ether that occurs in various types that differ in their degree of polymerization (molecular weight distribution) and degree of etherification. A particularly suitable ethyl cellulose can be obtained commercially, for example, under the trade name Aqualon® EC N 10 Ethylcellulose from the Ashland company.

$C_{6-30}$-alkylhydroxyethyl celluloses are cellulose compounds in which hydrophobic $C_{6-30}$-alkyl groups are attached to the cellulose skeleton via ethylene oxide units. Due to the introduction of $C_{6-30}$ alkyl groups on ethylene oxide units of the backbone, these celluloses exhibit a hydrophobic nature and are also called hydrophobically modified hydroxyethyl celluloses.

Cellulose is composed of β-1,4-glycosidic-linked d-glucopyranose units. In the solid state, crystalline regions in cellulose alternate with those of low order (amorphous regions). Natural and manufacturing-related impurities, such as the presence of carboxy groups, are typically in the range of approx. 1%. As contemplated herein, cellulose itself is therefore not considered an anionic polysaccharide.

Cellulose usable as contemplated herein has a degree of polymerization (DP), i.e., a chain length of glucopyranose units, of 10 to about 8000. However, it has been found that celluloses with a low degree of polymerization exert a positive effect on the dyeing properties of the agents.

So-called microcrystalline cellulose in particular shows beneficial effects in this respect. Microcrystalline cellulose is obtained by partial alkaline or acid hydrolysis of celluloses, in which only the amorphous regions of the semicrystalline cellulose are attacked and completely dissolved. This initially results in microfine cellulose, which is disaggregated into microcrystalline cellulose in aqueous suspension under the action of mechanical force.

The degree of polymerization remaining after hydrolysis (also called levelling-off degree of polymerization=LODP) of microcrystalline cellulose is in the range of approx. 30-400.

Preferred celluloses are therefore microcrystalline celluloses and have a degree of polymerization of about 30 to 400.

Thus, one embodiment as contemplated herein is exemplified in that the agent comprises microcrystalline cellulose as the cellulose.

Starch is a polysaccharide with the formula $(C_6H_{10}O_5)_n$, including α-D-glucose units. The macromolecule is one of the carbohydrates. Starch is one of the most important reserve substances in plant cells.

A starch usable as contemplated herein can be obtained, for example, from potatoes, corn, rice, peas, acorns, chestnuts, barley, wheat, bananas, sago, millet, sorghum, oats, rye, beans, batata, maranta or cassava.

In another preferred embodiment, an agent as contemplated herein is exemplified in that it comprises at least one polysaccharide (a3) selected from the group of potato starch, corn starch, rice starch, pea starch, acorn starch, chestnut starch, barley starch, wheat starch, rye starch, banana starch, sago starch, millet starch, sorghum starch, oat starch, bean starch, batata starch, maranta starch and cassava starch.

In a preferred embodiment, the agent as contemplated herein comprises at least one anionic polysaccharide. Within the group of anionic polysaccharides, the xanthans, alginates, carboxyalkyl celluloses and hyaluronic acids are particularly suitable.

In a particularly preferred embodiment, an agent as contemplated herein is exemplified in that it comprises at least one anionic polysaccharide (a3) selected from the group of xanthan gum, carboxyalkyl cellulose, alginic acid, carrageenan, tragacanth, karaya gum, gum arabic, gellan gum, pectin, agaropectin and/or salts thereof.

Xanthan is a polysaccharide which is composed of the structural components D-glucose, D-mannose, D-glucuronic acid, acetate and pyruvate, among others, and which is also known under the INCI name Xanthan Gum. Xanthan bears carboxy groups and is anionic or anionizable. Physiologically compatible salts of xanthan gum are also as contemplated herein.

Alginates (INCI designation algin) are the salts of alginic acid. Alginates are acidic polysaccharides containing carboxy groups, including D-mannuronic acid and D-guluronic acid in different ratios, which are linked with 1-4-glycosidic bonds. As contemplated herein, the alkali metal salts as well as the alkaline earth metal salts of the alpha acids are particularly suitable. The use of alginic acid, sodium alginate, potassium alginate, ammonium alginate and/or calcium alginate in the preparations as contemplated herein has proved particularly advantageous.

Carboxyalkyl celluloses are cellulose ethers in which the hydrogen atoms of the hydroxyl groups of cellulose are partially or completely substituted by carboxyalkyl groups. A preferred carboxyalkyl cellulose is carboxymethyl cellulose, which can preferably be used in the form of its sodium salt (sodium carboxymethyl cellulose) as an anionic polymer.

Basic building blocks of hyaluronic acid (INCI name hyaluronic acid, sodium hyaluronate) are an aminodisaccharide built up from D-glucuronic acid and N-acetylglucosamine in 1-3-glycosidic bond, which is β-1-4-glycosidically linked to the next unit. Sodium and potassium salts of hyaluronic acid have been found to be particularly suitable in the work leading to the present disclosure.

Carrageen is also known synonymously as carrageenan. Carrageenan is sulfated galactan that can be obtained, for example, by extraction from red algae. Carrageenan precipitated from the hot water extract of the algae is a colorless to sand-colored powder with a molecular weight of about 100000-800000 and a sulfate content of about 25%, which is very easily soluble in warm water. Carrageenan is divided into three main components with different properties, which are κ-carrageenan, κ-carrageenan and λ-carrageenan. The gel-forming x-fraction includes d-galactose-4-sulfate and 3,6-anhydro-α-d-galactose glycosidically linked alternately in the 1,3- and 1,4-positions. The non-gelling λ-fraction is composed of 1,3-glycosidically linked d-galactose-2-sulfate and 1,4-linked d-galactose-2,6-disulfate radicals and is readily soluble in cold water. The 1-carrageenan built up from d-galactose-4-sulfate in 1,3-bond and 3,6-anhydro-α-d-galactose-2-sulfate in 1,4-bond is soluble in hot water and gel-forming.

Within the group of anionic polysaccharides, xanthan gum has proven to be particularly suitable for achieving intense color results. Agents as contemplated herein containing xanthan (a3) are therefore explicitly very particularly preferred.

In an explicitly quite particularly preferred embodiment, an agent as contemplated herein is exemplified in that it contains at least one xanthan gum (a3).

The polysaccharide or polysaccharides, the preferred and especially preferred representatives described above, are preferably used in certain ranges of amounts in the agent as contemplated herein to achieve the best possible color intensity.

In this context, it has been found to be particularly preferred if the agent as contemplated herein contains—based on the total weight of the agent—one or more polysaccharides (a3) in a total amount of from about 0.1 to about 6.0 wt. %, preferably from about 0.5 to about 5.0 wt. %, more preferably from about 1.0 to about 4.0 wt. % and most preferably from about 1.5 to about 3.5 wt. %.

In a particularly preferred embodiment, an agent as contemplated herein is exemplified in that it contains—based on the total weight of the agent—one or more polysaccharides (a3) in a total amount of from about 0.1 to about 6.0 wt. %, preferably from about 0.5 to about 5.0 wt. %, more preferably from about 1.0 to about 4.0 wt. % and very particularly preferably from about 1.5 to about 3.5 wt. %.

In a particularly preferred embodiment, an agent as contemplated herein is exemplified in that it contains—based on the total weight of the agent—one or more nonionic polysaccharides (a3) in a total amount of from about 0.1 to about 6.0 wt. 00 preferably from about 0.5 to about 5.0 wt. %, more preferably from about 1.0 to about 4.0 wt. % and very particularly preferably from about 1.5 to about 3.5 wt. %.

In a particularly preferred embodiment, an agent as contemplated herein is exemplified in that it contains—based on the total weight of the agent—one or more anionic polysaccharides (a3) in a total amount of from 0.1 to about 6.0 wt. %, preferably from 0.5 to 5.0 wt. %, more preferably from 1.0 to 4.0 wt. % and very particularly preferably from 1.5 to 3.5 wt. %.

It is explicitly quite particularly preferred if the agent as contemplated herein contains—based on the total weight of the agent—about 0.1 to about 6.0 wt. %, preferably about 0.5 to about 5.0 wt. %, more preferably from about 1.0 to about 4.0 wt. % and very particularly preferably from about 1.5 to about 3.5 wt. % of hydroxyethyl cellulose.

It is further explicitly quite particularly preferred if the agent as contemplated herein contains—based on the total weight of the agent—about 0.1 to about 6.0 wt. %, preferably about 0.5 to about 5.0 wt. %, more preferably from about 1.0 to about 4.0 wt. % and very particularly preferably from about 1.5 to about 3.5 wt. % of hydroxypropyl cellulose.

It is further explicitly quite particularly preferred if the agent as contemplated herein contains—based on the total weight of the agent—about 0.1 to about 6.0 wt. %, preferably about 0.5 to about 5.0 wt. %, more preferably from about 1.0 to about 4.0 wt. % and very particularly preferably from about 1.5 to about 3.5 wt. % of xanthan. No silicone resins in the agent The work leading to the present disclosure has shown that the agents described above, which additionally contain at least one silicone resin, have significant disadvantages in terms of producing colorations with high color intensity. For this reason, the agent as contemplated herein is exemplified by being free of silicone resins.

A silicone resin as defined in the present disclosure is understood to be an MX resin, where "M" stands for a unit of Me3SiO and "Q" stands for a unit of $SiO_4$. Silicone resins thus comprise at least one, preferably several, "M" units and at least one, preferably several, Q units. Due to the $SiO_4$ unit, silicone resins are thus branched, in contrast to linear silicone polymers (a1).

For the further definition of silicone resins, please refer in full to EP 3058935 B1.

In other words, one of the objects of the present disclosure is an agent for coloring keratinous material, in particular human hair, containing
(a1) at least one linear amino-functionalized silicone polymer, and
(a2) at least one pigment, and
(a3) at least one polysaccharide,
and exemplified in that the agent is free from MQ silicone resins.

Examples of silicone resins are commercially available, for example, from Wacker®-Chemie AG, D-81737 Munich.

For example, the MQ silicone resin POWDER 803 TF is the product of co-hydrolysis of tetra alkoxy-silane (Q-unit) and trimethyl-ethoxysilane (M-unit) and can be understood as a three-dimensional network of a polysilicic acid blocked at the ends with trimethylsilyl moieties.

Other MQ silicone resins are also available from Dow® Corning. For example, Dow Corning@ MQ-1640 Flake Resin a combination of MQ and T propyl silicone resin and has the INCI designation: Trimethylsiloxysilicate (and) polypropylsilsesquioxane.

A mixture of amino silicone and MQ resin can also be purchased commercially, for example, in the form of the commercial product Belsil® ADM 8301 E from Wacker®; this substance bears the INCI designation amodimethicone/ morpholinomethyl silsesquioxane copolymer.

A feature of the agents as contemplated herein is that it does not contain the MQ resins described above, i.e., the total amount of all MQ silicone resins contained in the agent as contemplated herein—based on the total amount of the agent—is about 0 wt. %.

Fat Components (a4)

As a further optional component, the agent as contemplated herein can additionally contain at least one fat component (a4). It has been found that the use of at least one fatty ingredient (a4) results in the agent being in the form of an emulsion, which has the optimum viscosity and has also been found to be beneficial in terms of improving color intensity.

As contemplated herein, "fatty components" mean organic compounds with a solubility in water at room temperature (22° C.) and atmospheric pressure (760 mmHg) of less than about 1 wt. %, preferably less than about 0.1 wt. %. The definition of fat constituents explicitly covers only uncharged (i.e., non-ionic) compounds. Fat components have at least one saturated or unsaturated alkyl group with at least 12 C atoms. The molecular weight of the fat constituents is a maximum of about 5000 g/mol, preferably a maximum of about 2500 g/mol and particularly preferably a maximum of about 1000 g/mol. The fat components are neither polyoxyalkylated nor polyglycerylated compounds.

Very preferably, the fat constituents (a4) contained in the composition are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In the context of a further preferred embodiment, an agent as contemplated herein is exemplified in that it contains one or more fat constituents (a4) from the group of the $C_{12}$-$C_{30}$ fatty alcohols, the $C_{12}$-$C_{30}$ fatty acid triglycerides, the $C_{12}$-$C_{30}$ fatty acid monoglycerides, the $C_{12}$-$C_{30}$ fatty acid diglycerides and/or the hydrocarbons.

In this context, very particularly preferred fat constituents are understood to be constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. As contemplated herein, only non-ionic substances are explicitly regarded as fat components. Charged compounds such as fatty acids and their salts are not considered to be fat components.

The $C_{12}$-$C_{30}$ fatty alcohols can be saturated, mono- or polyunsaturated, linear or branched fatty alcohols with 12 to 30 C atoms.

Examples of preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

In a further preferred embodiment, an agent as contemplated herein is exemplified in that it comprises one or more $C_{12}$-$C_{30}$ fatty alcohols (a4) selected from the group of Dodecan-1-ol (dodecyl alcohol, lauryl alcohol),
Tetradecan-1-ol (tetradecyl alcohol, myristyl alcohol),
Hexadecan-1-ol (hexadecyl alcohol, cetyl alcohol, palmityl alcohol),
Octadecan-1-ol (octadecyl alcohol, stearyl alcohol),
Arachyl alcohol (eicosan-1-ol),
Heneicosyl alcohol (heneicosan-1-ol),
Behenyl alcohol (docosan-1-ol),
(9Z)-Octadec-9-en-1-ol (oleyl alcohol),
(9E)-Octadec-9-en-1-ol (elaidyl alcohol),
(9Z,12Z)-Octadeca-9,12-dien-1-ol (linoleyl alcohol),
(9Z,12Z,15Z)-Octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-Octyl-dodecanol,
2-hexyl dodecanol and/or
2-Butyl-dodecanol contains.

It has been found to be particularly preferable to use one or more $C_{12}$-$C_{30}$ fatty alcohols (a4) in specific ranges of amounts.

It is particularly preferred if the composition contains one or more $C_{12}$-$C_{30}$ fatty alcohols in a total amount of from about 2.0 to about 50.0 wt. %, preferably from about 3.0 to about 30.0 wt. %, more preferably from about 4.0 to about 20.0 wt. %, still more preferably from about 5.0 to about 15.0 wt. % and most preferably from about 5.0 to about 10.0 wt. %, based on the total weight of the composition.

Further, as a suitable fat ingredient, the composition (a4) may also contain at least one $C_{12}$-$C_{30}$ fatty acid triglyceride that is $C_{12}$-$C_{30}$ fatty acid monoglyceride and/or $C_{12}$-$C_{30}$ fatty acid diglyceride. As contemplated herein, a $C_{12}$-$C_{30}$ fatty acid triglyceride is understood to be the triester of the trivalent alcohol glycerol with three equivalents of fatty acid. Both structurally identical and different fatty acids within a triglyceride molecule can be involved in the formation of esters.

As contemplated herein, fatty acids are to be understood as saturated or unsaturated, unbranched or branched, unsubstituted or substituted $C_{12}$-$C_{30}$ carboxylic acids. Unsaturated fatty acids can be mono- or polyunsaturated. For an unsaturated fatty acid, its C=C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/ornervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, moringa oil, apricot kernel oil, marula oil and/or optionally hardened castor oil are particularly suitable for use in the product as contemplated herein.

A $C_{12}$-$C_{30}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{30}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{30}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/ornervonic acid [(15Z)-tetracos-15-enoic acid].

Particularly good results were obtained when agent (B) contained at least one $C_{12}$-$C_{30}$ fatty acid monoglyceride selected from the monoesters of glycerol with one equivalent of fatty acid selected from the group of dodecanoic acid (lauric acid), Tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

In the context of a further embodiment, a composition as contemplated herein is exemplified in that it comprises at least one $C_{12}$-$C_{30}$ fatty acid monoglyceride selected from the monoesters of glycerol with one equivalent of fatty acid from the group of dodecanoic acid, tetradecanoic acid, hexadecanoic acid, tetracosanoic acid, octadecanoic acid, eicosanoic acid and/or docosanoic acid.

It has been shown to be preferable to use one or more $C_{12}$-$C_{30}$ fatty acid mono-, $C_{12}$-$C_{30}$ fatty acid di- and/or $C_{12}$-$C_{30}$ fatty acid triglycerides (a4) in specific ranges of amounts in the composition.

With regard to the solution of the problem as contemplated herein, it has proved advantageous if the composition—based on the total weight of the composition—contained one or more $C_{12}$-$C_{30}$ fatty acid mono-, $C_{12}$-$C_{30}$ fatty acid di- and/or $C_{12}$-$C_{30}$ fatty acid triglycerides (a4) in a total amount of about 0.1 to about 20.0 wt.-%, preferably from about 0.3 to about 15.0 wt. %, more preferably from about 0.5 to about 10.0 wt. % and most preferably from about 0.8 to about 5.0 wt. %.

In a very particularly preferred embodiment, a process as contemplated herein is exemplified in that the composition contains—based on the total weight of the composition—one or more $C_{12}$-$C_{30}$ fatty acid mono-, $C_{12}$-$C_{30}$ fatty acid di- and/or $C_{12}$-$C_{30}$ fatty acid triglycerides in a total amount of from about 0.1 to about 20.0 wt. %, preferably from about 0.3 to about 15.0 wt. %, more preferably from about 0.5 to about 10.0 wt. % and very particularly preferably from about 0.8 to about 5.0 wt. %.

The $C_{12}$-$C_{30}$ fatty acid mono-, $C_{12}$-$C_{30}$ fatty acid di- and/or $C_{12}$-$C_{30}$ fatty acid triglycerides may be used as the sole fat components (a4) in the compositions. However, it may also be suitable as contemplated herein to incorporate at least one $C_{12}$-$C_{30}$ fatty acid mono-, $C_{12}$-$C_{30}$ fatty acid di- and/or $C_{12}$-$C_{30}$ fatty acid triglyceride in combination with at least one $C_{12}$-$C_{30}$ fatty alcohol into the composition.

Furthermore, as a very particularly preferred fatty constituent (a4), the composition may also contain at least one hydrocarbon.

Hydrocarbons are compounds formed exclusively of the atoms carbon and hydrogen with 8 to about 80 C atoms. In this context, aliphatic hydrocarbons such as mineral oils, liquid paraffin oils (e.g., Paraffinum Liquidum or Paraffinum Perliquidum), isoparaffin oils, semi-solid paraffin oils, paraffin waxes, hard paraffin (Paraffinum Solidum), Vaseline® and polydecenes are particularly preferred.

Liquid paraffin oils (Paraffinum Liquidum and Paraffinum Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, including hydrocarbon chains with a C-chain distribution of about 25 to about 35 C-atoms.

Very particularly satisfactory results were obtained when the composition contained at least one hydrocarbon (a4) selected from the group of mineral oils, liquid kerosene oils, isoparaffin oils, semisolid kerosene oils, kerosene waxes, hard kerosene (Paraffinum solidum), petrolatum and polydecenes.

In a very particularly preferred embodiment, a composition as contemplated herein is exemplified in that it comprises at least one fatty constituent (a4) from the group of hydrocarbons.

Regarding the solution of the problem as contemplated herein, it proved to be quite particularly preferable if the composition contained—based on the total weight of the composition—one or more hydrocarbons (a4) in a total amount of from about 0.5 to about 20.0 wt. %, preferably from about 0.7 to about 10.0 wt. %, more preferably from about 0.9 to about 5.0 wt. % and most preferably from about 1.0 to about 4.0 wt. %.

In a very particularly preferred embodiment, an agent as contemplated herein is exemplified in that it contains—based on the total weight of the agent—one or more hydrocarbons (a4) in a total amount of in a total amount of from about 0.5 to about 20.0 wt. %, preferably from about 0.7 to about 10.0 wt. %, more preferably from about 0.9 to about 5.0 wt. % and very particularly preferably from about 1.0 to about 4.0 wt. %.

The hydrocarbon(s) may be used as the sole fatty ingredients (a4) in the compositions. However, it is also as contemplated herein to incorporate at least one hydrocarbon in combination with at least one other constituent into the agents.

Very preferably, the composition contains at least one fatty constituent (a4) from the group of $C_{12}$-$C_{30}$ fatty alcohols and at least one further fatty constituent from the group of hydrocarbons.

Water Content in Agent

The agent described above is a ready-to-use agent that can be applied to the keratinous material. This ready-to-use agent preferably has a high water content. It has been found that particularly suitable agents are those containing—based on the total weight of the agent—about 50.0 to about 98.0 wt. %, preferably about 60.0 to about 90.0 wt. %, more preferably about 70.0 to about 90.0 wt. % and most preferably about 75.0 to about 90.0 wt. % of water.

In a further explicitly quite particularly preferred embodiment, an agent as contemplated herein is exemplified in that it contains—based on the total weight of the agent—about 50.0 to about 98.0 wt. %, preferably about 60.0 to about 90.0 wt. %, further preferably about 70.0 to about 90.0 wt. % and very particularly preferably about 75.0 to about 90.0 wt. % of water.

Surfactants in the Agent

Due to its content of water and fat constituent (a4), the agent as contemplated herein is particularly preferably in the form of an emulsion. To further optimize the formation of the emulsion, it has proven particularly preferable to continue to use at least one surfactant in the agent.

Very preferably, therefore, the composition additionally contains at least one surfactant.

In the context of a further particularly preferred embodiment, an agent as contemplated herein is exemplified in that it comprises at least one surfactant, The term surfactants (T) refer to surface-active substances that can form adsorption layers on surfaces and interfaces or aggregate in bulk phases to form micelle colloids or lyotropic mesophases. A distinction is made between anionic surfactants including a hydrophobic radical and a negatively charged hydrophilic head group, amphoteric surfactants, which carry both a negative and a compensating positive charge, cationic surfactants, which in addition to a hydrophobic radical have a positively charged hydrophilic group, and non-ionic surfactants, which have no charges but strong dipole moments and are strongly hydrated in aqueous solution.

In a very particularly preferred embodiment, an agent as contemplated herein is exemplified in that it comprises at least one anionic and/or nonionic surfactant.

Suitable anionic surfactants that may be used in the agents as contemplated herein include:
linear and branched fatty acids with 8 to 30 C atoms (Soaps),
Ether carboxylic acids of the formula R—O—($CH_2$—$CH_2O$)$_x$—$CH_2$—COOH, in which R is a linear or branched, saturated or unsaturated alkyl group having 8 to about 30 C atoms and x=0 or 1 to about 16

Acylsarcosides with 8 to about 24 C atoms in the acyl group,
Acyltaurides with 8 to about 24 C atoms in the acyl group,
Acyl isethionates with 8 to about 24 C atoms in the acyl group,
Sulfosuccinic acid mono- and/or dialkyl esters with 8 to about 24 C atoms in the alkyl group and sulfosuccinic acid mono-alkyl polyoxyethyl esters with 8 to about 24 C atoms in the alkyl group and 1 to 6 oxyethyl groups,
Alpha-olefin sulfonates with 8 to about 24 C atoms,
Alkyl sulfate and/or alkyl polyglycol ether sulfate salts of the formula R—($OCH_2$—$CH_2$)$_x$—$OSO_3^-$$X^{30}$, in which R is a preferably linear or branched, saturated or unsaturated alkyl group having 8 to about 30 carbon atoms, x=0 or 1 to about 12 and X is an alkali metal or ammonium ion,
Sulfonates of unsaturated fatty acids with 8 to about 24 C atoms and 1 to 6 double bonds, Esters of tartaric acid and citric acid with alcohols, which are addition products of about 2-15 molecules of ethylene oxide and/or propylene oxide to fatty alcohols with 8 to about 22 C atoms, and
Alkyl and/or alkenyl ether phosphates of the formula,

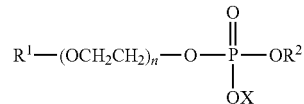

where $R^1$ is preferably an aliphatic hydrocarbon radical of 8 to about 30 carbon atoms, $R^2$ is hydrogen, a radical ($CH_2CH_2O$)$_n R^1$ or X, n is from 0 to 10 and X is hydrogen, an alkali metal or alkaline earth metal or $NR^3R^4R^5R^6$, where $R^3$ to $R^6$ are each independently of the others a $C_1$- to $C_4$-hydrocarbon radical.

Non-ionic surfactants contain, for example, a polyol group, a polyalkylene glycol ether group or a combination of polyol and polyglycol ether group as the hydrophilic group. Such links include
Addition products of about 2 to about 50 mol ethylene oxide and/or 0 to about 5 mol propylene oxide to linear and branched fatty alcohols with 6 to about 30 C atoms, the fatty alcohol polyglycol ethers or the fatty alcohol polypropylene glycol ethers or mixed fatty alcohol polyethers,
Addition products of about 2 to about 50 mol ethylene oxide and/or 0 to about 5 mol propylene oxide to linear and branched fatty acids with 6 to about 30 C atoms, the fatty acid polyglycol ethers or the fatty acid polypropylene glycol ethers or mixed fatty acid polyethers,
Addition products of about 2 to about 50 mol ethylene oxide and/or 0 to about 5 mol propylene oxide to linear and branched alkylphenols having 8 to about 15 C atoms in the alkyl group, the alkylphenol polyglycol ethers or the alkylpolypropylene glycol ethers or mixed alkylphenol polyethers,
Addition products of about 2 to about 50 moles of ethylene oxide and/or 0 to about 5 moles of propylene oxide to linear and branched fatty alcohols having 8 to about 30 carbon atoms, to fatty acids, end-capped with a methyl or $C_2$-$C_6$-alkyl radical 8 to about 30 carbon atoms and on alkyl phenols with 8 to about 15 carbon atoms in the alkyl group, such as the types available under the sales names Dehydol® LS and Dehydol® LT (Cognis), C$_{12}$-C$_{30}$ fatty acid mono- and diesters of addition products of about 1 to about 30 mol ethylene oxide to glycerol, Addition products of about 5 to about 60 mol ethylene oxide to castor oil and hardened castor oil, Polyol fatty acid esters, such as the commercial product Hydagen® HSP (Cognis) or Sovermol® grades (Cognis), alkoxylated triglycerides, alkoxylated fatty acid alkyl esters of the formula (Tnio-1)

$$R^1CO-(OCH_2CHR^2)_w OR^3 \qquad \text{(Tnio-1)}$$

in which R$^1$CO is a linear or branched, saturated and/or unsaturated acyl radical having 6 to about 22 carbon atoms, R2 is hydrogen or methyl, R$^3$ is linear or branched alkyl radicals having 1 to 4 carbon atoms and w is numbers from 1 to about 20, amine oxides, Hydroxy mixed ethers, as described for example in DE-OS 19738866, Sorbitan fatty acid esters and addition products of ethylene oxide to sorbitan fatty acid esters such as polysorbates, Sugar fatty acid esters and addition products of ethylene oxide to sugar fatty acid ester, Addition products of ethylene oxide to fatty acid alkanolamides and fatty amines, Sugar tensides of the alkyl and alkenyl oligoglycoside type according to formula (E4-II), $$R^4O-[G]_p \qquad \text{(Tnio-2)}$$

in which R$^4$ is an alkyl or alkenyl radical containing 4 to about 22 carbon atoms, G is a sugar residue containing 5 or 6 carbon atoms and p is a number of 1 to 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula (Tnio-2) indicates the degree of oligomerization (DP), i.e. the distribution of mono- and oligoglycosides and stands for a number between 1 and 10. While p must always be an integer in the individual molecule and can assume the values p=1 to 6, the value p for a certain alkyl oligoglycoside is an analytically determined arithmetical quantity, which usually represents a fractional number. Preferably alkyl and/or alkenyl oligoglycosides with an average degree of oligomerization p of about 1.1 to about 3.0 are used. From an application technology point of view, those alkyl and/or alkenyl oligoglycosides are preferred whose degree of oligomerization is less than about 1.7 and lies between about 1.2 and about 1.4. The alkyl or alkenyl radical R$^4$ can be derived from primary alcohols containing 4 to 11, preferably 8 to 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or during the hydrogenation of aldehydes from Roelen's oxo synthesis. Preferred are alkyl oligoglucosides with a chain length of C$_5$-C$_{10}$ (DP=1 to 3), which are obtained as a preliminary step in the distillative separation of technical C$_8$-C$_{18}$ coconut-fatty alcohol and may be contaminated with less than about 6 wt. % of C$_{12}$ alcohol, and alkyl oligoglucosides based on technical C$_{9/11}$ oxoalcohols (DP=1 to 3). The alkyl or alkenyl radical R$^{15}$ can also be derived from primary alcohols having 12 to about 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Preferred are alkyl oligoglucosides based on hardened C$_{12/14}$ coconut alcohol with a DP of 1 to 3.

Sugar surfactants of the fatty acid N-alkyl polyhydroxyalkylamide type, a nonionic surfactant of formula (Tnio-3)

$$R^5CO-NR^6-[Z] \qquad \text{(Tnio-3)}$$

in which R$^5$CO is an aliphatic acyl radical containing 6 to about 22 carbon atoms, R$^6$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups. The fatty acid N-alkyl polyhydroxyalkylamides are known substances that can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkyl polyhydroxyalkylamides are preferably derived from reducing sugars with 5 or 6 carbon atoms, especially from glucose. The preferred fatty acid N-alkyl polyhydroxyalkylamides are therefore fatty acid N-alkylglucamides as represented by the formula (Tnio-4):

$$R^7CO-(NR^8)-CH_2-[CH(OH)]_4-CH_2OH \qquad \text{(Tnio-4)}$$

Preferably, glucamides of the formula (Tnio-4) are used as fatty acid-N-alkyl polyhydroxyalkylamides, in which R$^8$ represents hydrogen or an alkyl group and RCO represents the acyl radical of caproic acid, caprylic acid, capric acid, Lauric acid, myristic acid, palmitic acid, palmoleic acid, stearic acid, isostearic acid, oleic acid, elaidic acid, petroselinic acid, linoleic acid, linolenic acid, arachidic acid, gadoleic acid, behenic acid or erucic acid or their technical mixtures. Particularly preferred are fatty acid N-alkyl glucamides of the formula (Tnio-4), which are obtained by reductive amination of glucose with methylamine and subsequent acylation with lauric acid or C$_{12/14}$ coconut fatty acid or a corresponding derivative. Furthermore, polyhydroxyalkylamides can also be derived from maltose and palatinose.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with about 2 to about 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R contains 6 to about 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, and 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

The surfactant(s) may be present in the agent in a total amount—based on the total weight of the agent—of from about 0.1 to about 18.0 wt. %, preferably from about 0.5 to about 16.0 wt. %, more preferably from about 1.0 to about 14.0 wt. % and most preferably from about 1.5 to about 12.0 wt. %.

Other Optional Ingredients in the Agent

In addition to the ingredients (a1) to (a3) essential to the present disclosure already described, the agent may also contain further optional ingredients.

The agents may also contain other active ingredients, auxiliaries and additives, such as solvents, structurants such as glucose, maleic acid and lactic acid, hair-conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; Ceramides or pseudoceramides; vitamins, provitamins and vitamin precursors; plant extracts; fats and waxes such as fatty alcohols, beeswax, montan wax and kerosene; Swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of about 0.0001 to about 25 wt. % each, about 0.0005 to about 15 wt. %, based on the total weight of the respective agent.

Agent pH value

The pH values of the agent as contemplated herein can be adjusted to a slightly acidic to alkaline pH. Very preferably, colorant (F) has a pH value in the range from about 5.0 to about 10.0, preferably from about 6.0 to about 9.5, more preferably from about 6.0 to about 8.7, and most preferably from about 6.0 to about 7.5.

Alkalizing agents and acidifying agents known to those skilled in the art can be used to set the respective desired pH values. The pH values for the purposes of the present disclosure are pH values measured at a temperature of 22° C.

As alkalizing agents, the agents may contain, for example, ammonia, alkanolamines and/or basic amino acids.

The alkanolamines which can be used in the agent as contemplated herein are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, and 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore exemplified in that the agent as contemplated herein contains an alkanolamine selected from 2-aminoethan-1-ol and/or 2-amino-2-methylpropan-1-ol as alkalizing agent.

As contemplated herein, an amino acid is an organic compound containing at least one protonatable amino group and at least one —COOH or —$SO_3H$ group in its structure. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than 7.0.

Basic α-amino carboxylic acids contain at least one asymmetric carbon atom. As contemplated herein, both enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein is therefore exemplified in that the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Also, as contemplated herein, the desired pH value can be adjusted by employing a buffer system. A buffer or buffer system is usually understood to be a mixture of a weak or medium-strength acid (e.g., acetic acid) with a completely dissociated neutral salt of the same acid (e.g., sodium acetate). If some base or acid is added, the pH value hardly changes (buffering). The effect of the buffer substances contained in a buffer solution is based on the scavenging reaction of hydrogen or hydroxide ions with the formation of weak acids or bases due to their dissociation equilibrium.

A buffer system can be formed from a mixture of an inorganic or organic acid and a corresponding salt of that acid.

Acids can be buffered by all salts of weak acids and strong bases, bases by salts of strong acids and weak bases. The strong hydrochloric acid (completely dissociated into ions) can be buffered, for example, by adding sodium acetate. According to the balance

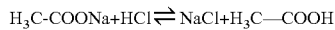

hydrochloric acid is converted by sodium acetate to the weak acetic acid with the formation of sodium chloride, which dissociates only to a small extent in the presence of an excess of sodium acetate. Buffers that are effective against both acids and bases are mixtures of weak acids and their salts.

Examples of buffer systems known from the literature are acetic acid/sodium acetate, boric acid/sodium borate, phosphoric acid/sodium phosphate and hydrogen carbonate/soda.

The pH of the agent as contemplated herein can be adjusted, for example, by adding an inorganic or organic buffer system. For the purposes of the present disclosure, an inorganic buffer system is understood to be a mixture of an inorganic acid and its conjugate corresponding inorganic base.

For the purposes of the present disclosure, an organic buffer system is understood to be a mixture of an organic acid and its conjugate corresponding base. Due to the organic acid radical, the conjugate corresponding base of the organic acid is also organic. Here, the cation presents to neutralize the charge of the acid anion can be inorganic or organic.

Examples of inorganic acids are sulfuric acid, hydrochloric acid and phosphoric acid ($H_3PO_4$). Phosphoric acid is a medium-strength acid that is particularly preferred.

A particularly well-suited inorganic acid is potassium dihydrogen phosphate. Potassium dihydrogen phosphate has the molecular formula $KH_2PO_4$ and carries the CAS number 7778-77-0. Potassium dihydrogen phosphate has a molar mass of 136.09 g/mol. It is highly soluble in water (222 g/l at 20° C.) and reacts acidically in water. A 5% solution of potassium dihydrogen phosphate in water has a pH value of about 4.4.

Another particularly suitable inorganic acid is sodium dihydrogen phosphate. Sodium dihydrogen phosphate has the molecular formula $NaH_2PO_4$ and carries the CAS numbers 7558-80-7 (anhydrate), 10049-21-5 (monohydrate) and 13472-35-0 (dihydrate). The anhydrous sodium dihydrogen phosphate has a molar mass of 119.98 g/mol. Sodium dihydrogen phosphate reacts acidically in aqueous solution.

Particularly preferred as a corresponding salt of the above two acids are dipotassium hydrogen phosphate. Dipotassium hydrogen phosphate has the molecular formula $K_2HPO_4$ and carries the CAS numbers 7758-11-4 (anhydrous) and 16788-57-1 (trihydrate). The anhydrous dipotassium hydrogen phosphate has a molar mass of 174.18 g/mol. Dipotassium hydrogen phosphate reacts alkaline in aqueous solution.

Also particularly preferred as a corresponding salt of the above two acids are disodium hydrogen phosphate. Disodium hydrogen phosphate has the molecular formula $Na_2HPO_4$ and carries the CAS numbers 7558-79-4 (anhydrous), 10028-24-7 (dihydrate), 7782-85-6 (heptahydrate) and 10039-32-4 (dodecahydrate). Anhydrous disodium hydrogen phosphate has a molar mass of 141.96 g/mol. Disodium hydrogen phosphate reacts alkaline in aqueous solution.

Examples of organic acids are citric acid, succinic acid, tartaric acid, lactic acid, acetic acid, malic acid, malonic acid and maleic acid.

Examples of the corresponding salts of these organic acids are the sodium and potassium salts of citric acid, the sodium and potassium salts of succinic acid, the sodium and potassium salts of tartaric acid, sodium and potassium salts of lactic acid, sodium and potassium salts of acetic acid, sodium and potassium salts of malic acid, sodium and potassium salts of malonic acid and sodium and potassium salts of maleic acid.

Process for Dyeing Keratin Material

The agents described above can be excellently used in processes for dyeing keratinous material, especially human hair.

A second object of the present disclosure is therefore a method for coloring keratinous material, in particular human hair, comprising the following steps:

(1) Application of a coloring agent to the keratinous material, wherein the coloring agent is an agent as disclosed in detail in the description of the first subject matter of the present disclosure, (2) Exposure of the colorant to the keratinous material and (3) Rinse out the colorant with water.

In step (1) of the process as contemplated herein, the agent of the first portion of the present is applied to the keratinous material, which is most preferably human hair.

In step (2) of the process as contemplated herein, the agent is then allowed to act on the keratinous material after its application. In this context, different exposure times of, for example, about 30 seconds to about 60 minutes are conceivable.

However, a major advantage of the dyeing system as contemplated herein is that an intensive color result can be achieved even in short periods after short exposure times. For this reason, it is advantageous if the application mixture remains on the keratin material only for comparatively short periods of time after its application, from about 30 seconds to about 15 minutes, preferably from about 30 seconds to about 10 minutes, and particularly preferably from about 1 to about 5 minutes.

In a further preferred embodiment, a method as contemplated herein is exemplified by:

(2) Exposure of the colorant to the keratinous material for a period ranging from about 30 seconds to about 15 minutes, preferably from about 30 seconds to about 10 minutes, and most preferably from about 1 to about 5 minutes.

Finally, following the action of the application mixture on the keratin material, it is rinsed with water in step (3) of the process.

Here, in one embodiment, the application mixture can be washed out with water only, i.e., without the aid of an after-treatment agent or a shampoo. The use of a post-treatment agent or conditioner in step (6) is also conceivable in principle.

However, to solve the task as contemplated herein and to increase the convenience of use, it has proved particularly preferable to rinse the agent in step (3) exclusively with water without the aid of a further after-treatment agent, shampoo or conditioner.

In a further preferred embodiment, a method as contemplated herein is exemplified by:

(3) Rinse out the dye with water only.

Concerning the further preferred embodiments of the method as contemplated herein, mutatis mutandis what has been said about the agents according to the present disclosure applies.

Examples

1. Formulations

The following formulations were prepared (all data in wt. % unless otherwise stated):

| | Colorants | | | |
|---|---|---|---|---|
| | (V1) | (V2) | (E1) | (E2) |
| Cetyl alcohol | 3.0 | 3.0 | 3.0 | 3.0 |
| $C_{12}$-$C_{18}$-fatty alcohols (Lorol ® techn.) | 3.0 | 3.0 | 3.0 | 3.0 |
| Phenoxyethanol | 0.9 | 0.9 | 0.9 | 0.9 |
| Sodium salicylate | 0.4 | 0.4 | 0.4 | 0.4 |
| Unipure ® Red LC 3071 (CI 15850) | 1.0 | 1.0 | 1.0 | 1.0 |
| Dow ® Corning 2-8566 (siloxanes and silicones, 3-[(2-aminoethyl)amino]-2-methylpropyl Me, di-Me-siloxane. | 1.0 | — | 1.0 | 1.0 |
| Belsil ® ADM 8301 E (amodimethicone/morpholinomethyl silsesquioxane copolymer, Wacker ®) | — | 1.0 | — | — |
| 1.2-propanediol | 10.0 | 10.0 | 10.0 | 10.0 |
| Potassium dihydrogen phosphate | 0.35 | 0.35 | 0.35 | 0.35 |
| Disodium hydrogen phosphate | 0.72 | 0.72 | 0.72 | 0.72 |
| Emuglade CM (BASF ®, cetearyl isononanoate, ceteareth-20, cetearyl alcohol, glyceryl stearate, glycerin, ceteareth-12, cetyl palmitate). | 3.0 | 3.0 | 3.0 | 3.0 |
| Natrosol ® 250 HR (hydroxyethyl cellulose) | — | — | 2.0 | — |
| Keltrol ® CG-SFT (CP, Kelco ®, Xanthan Gum) | — | 2.0 | — | 2.0 |
| Water | ad 100 | ad 100 | ad 100 | ad 100 |

2. Application

The previously prepared agents were applied to hair strands (Kerling, Euronatural hair white liquor ratio: 1 g of colorant (E1) per g of hair strand) applied. The agent was left to act for five minutes. Subsequently, the hair strand was thoroughly washed (1 minute) with water, dried and then colorimetrically measured with a colorimeter from Datacolor®, type Spectraflash 450.

The dE value used to evaluate the different color intensities is derived from the L*a*b* colorimetric values measured on the respective strand part as follows:

$$dE=[(L_i-L_0)^2+(a_i-a_0)^2+(b_i-b_0)]^2$$

$L_0$, $a_0$ and $b_0$=measured values of the uncolored strand
$L_i$, $a_i$ and $b_i$=measured values of the strand dyed with The larger the dE value, the higher the color distance between undyed and dyed strands and the higher the color intensity.

| | Agent | | | |
|---|---|---|---|---|
| | L | a | b | dE |
| Kerling, uncolored | 73.18 | 2.35 | 22.09 | — |
| Comparison (V1) | 44.17 | 45.43 | 7.40 | 53.97 |
| Comparison (V2) | 65.32 | 11.00 | 8.50 | 17.92 |
| Present disclosure (E1) | 38.11 | 45.76 | 9.03 | 57.31 |
| Present disclosure (E2) | 39.98 | 46.67 | 9.39 | 56.81 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratinous material, comprising
   (a1) at least one linear amino-functionalized silicone polymer, and
   (a2) at least one pigment, wherein the at least one pigment (a2) comprises a pigment selected from the group of colored metal oxides, metal hydroxides, metal oxide hydrates, silicates, metal sulfides, complex metal cyanides, metal sulfates, bronze pigments, mica- or mica-based colored pigments coated with at least one metal oxide and/or a metal oxychloride, carmine, quinacridone, phthalocyanine, sorghum, blue pigments with the color index numbers CI 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470, and combinations thereof, and
   (a3) at least one polysaccharide,
   wherein the agent is free of silicone resins.

2. The agent according to claim 1, wherein the at least one linear, amino-functionalized silicone polymer (a1) comprises at least one secondary amino group.

3. The agent according to claim 1, wherein the at least one linear amino-functionalized silicone polymer (a1) comprises at least one structural unit of the formula (Si amino),

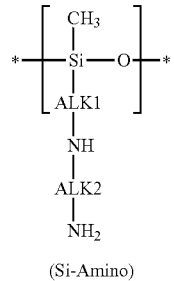

(Si-Amino)

where
   ALK1 and ALK2 independently represent a linear or branched $C_1$-$C_{20}$ divalent alkylene group.

4. The agent according to claim 1, wherein the at least one linear amino-functionalized silicone polymer (a1) comprises structural units of a formula (Si-I) and of a formula (Si-II)

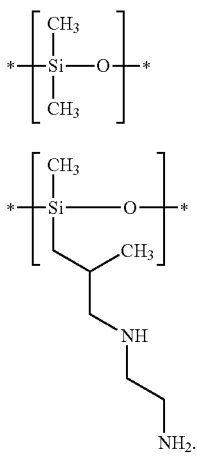

(Si-I)

(Si-II)

5. The agent according to claim 1, wherein the agent comprises—based on a total weight of the agent—the one or more linear, amino-functionalized silicone polymers (a1) in a total amount of from about 0.1 to about 8.0 wt. %.

6. The agent according to claim 1, wherein the agent comprises—based on a total weight of the agent—the one or more pigments (a2) in a total amount of from about 0.01 to about 10.0 wt. %.

7. The agent according to claim 1, wherein the at least one polysaccharide (a3) comprises a polysaccharide selected from the group of nonionic polysaccharides, anionic polysaccharides and cationic polysaccharides.

8. The agent according to claim 1, wherein the at least one nonionic polysaccharide (a3) comprises a polysaccharide selected from the group of hydroxy-$C_1$-$C_{30}$-alkylcelluloses, hydroxy-$C_1$-$C_{30}$-alkylmethylcelluloses, hydroxy-$C_1$-$C_{30}$-alkylethylcelluloses, $C_1$-$C_{30}$-alkylcelluloses, $C_6$-$C_{30}$-alkylhydroxyethylcelluloses, cellulose, starch, and combinations thereof.

9. The agent according to claim 1, wherein the at least one anionic polysaccharide (a3) comprises a polysaccharide selected from the group of xanthan gum, carboxyalkyl cellulose, alginic acid, carrageenan, tragacanth, karaya gum, gum arabic, gellan gum, pectin, agaropectin and/or salts thereof.

10. The agent according to claim 1, wherein the agent comprises—based on a total weight of the agent—the one or more polysaccharides (a3) in a total amount of about 0.1 to about 6.0 wt. %.

11. The agent according to claim 1, wherein the agent comprises one or more fat constituents selected from the group of $C_{12}$-$C_{30}$ fatty alcohols, $C_{12}$-$C_{30}$ fatty acid triglycerides, $C_2$-$C_{30}$ fatty acid monoglycerides, $C_{12}$-$C_{30}$ fatty acid diglycerides, hydrocarbons, and combinations thereof.

12. A method for dyeing keratinous material, the method comprising the following steps:
(1) to the keratinous material, wherein the agent comprises (a1) a linear amino-functionalized silicone polymer (a1), a pigment (a2), and a polysaccharide (a3), wherein the agent is free of silicone resins,
(2) exposing the agent to the keratinous material and
(3) rinsing the agent out of the keratinous material with water.

13. The method according to claim 12, comprising:
(2) exposing the agent to the keratinous material for a period ranging from about 30 seconds to about 15 minutes.

14. The agent according to claim 1, wherein the at least one linear amino-functionalized silicone polymer (a1) comprises structural units of a formula (Si-V)

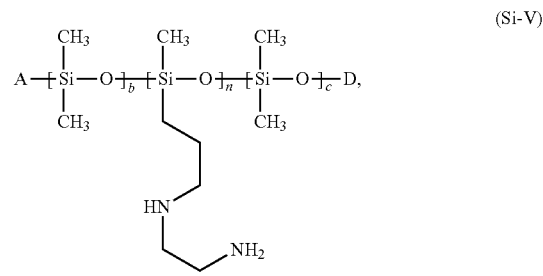

(Si-V)

wherein
A represents a group —OH, —O-Si(CH$_3$)$_3$,O-Si(CH$_3$)$_2$OH , —O-Si(CH$_3$)$_2$OCH$_3$,
D represents a group —H, —Si(CH$_3$)$_3$,—Si(CH$_3$)$_2$OH, —Si(CH$_3$)$_2$OCH$_3$, b, n, and c stand for integers between 0 and about 1000, with the specifications n>0 and b+c>0, and wherein
at least one of the conditions A=−OH or D=−H is fulfilled.

15. The agent according to claim 1, wherein the agent comprises–based on a total weight of the agent–the one or more linear, amino-functionalized silicone polymers (a1) in a total amount of from about 0.4 to about 2.5 wt. %.

16. The agent according to claim 1, wherein the agent comprises—based on a total weight of the agent—the one or more pigments (a2) in a total amount of from about 0.25 to about 1.5 wt. %.

17. The agent according to claim 1, wherein the agent comprises—based on a total weight of the agent—the one or more polysaccharides (a3) in a total amount of about 1.5 to about 3.5 wt. %.

18. The method according to claim 12, comprising:
(2) exposing the agent to the keratinous material for a period ranging from about 1 minute to about 5 minutes.

* * * * *

UNITED STATES PATENT AND TRADEMARK OFFICE
CERTIFICATE OF CORRECTION

PATENT NO. : 11,957,779 B2
APPLICATION NO. : 17/780003
DATED : April 16, 2024
INVENTOR(S) : Constanze Kruck et al.

It is certified that error appears in the above-identified patent and that said Letters Patent is hereby corrected as shown below:

In the Specification

Column 3, Line 60 change "105 g/mol" to --$10^5$ g/mol--
Column 9, Line 32 change "R'$_a$G$_{3-a}$-Si(OSIG$_2$)$_n$-(OSiG$_b$R'$_{2-6}$)$^m$-O-SiG$_{3-a}$-R'$_a$" to --R'$_a$G$_{3-a}$-Si(OSIG$_2$)$_n$-(OSiG$_b$R'$_{2-6}$)$_m$-O-SiG$_{3-a}$-R'$_a$--
Column 16, Line 7 change "COLIPA no B001" to --COLIPA n° B001--
Column 16, Line 8 change "COLIPA no: C54" to --COLIPA n° C54--
Column 16, Line 10 change "COLIPA no C29" to --COLIPA n° B001--
Column 16, Line 16 change "COLIPA no C015" to --COLIPA n° C015--
Column 16, Line 30 change "Red no106" to --Red n° 106--
Column 16, Line 32 change "COLIPA no C$_{53}$" to --COLIPA n° C$_{53}$--
Column 16, Line 47 change "Black no 401" to --Black n° 401--
Column 16, Line 49 change "COLIPA no B15" to --COLIPA n° B15--
Column 22, Line 33 change "Me3SiO" to --Me$_3$SiO--
Column 24, Line 44 change "C=C" to --C-C--

Signed and Sealed this
Twenty-second Day of October, 2024

*Katherine Kelly Vidal*

Katherine Kelly Vidal
*Director of the United States Patent and Trademark Office*